US011533435B2

United States Patent
Crabtree et al.

(10) Patent No.: US 11,533,435 B2
(45) Date of Patent: Dec. 20, 2022

(54) MULTIFUNCTIONAL CAMERA SYSTEM FOR VIDEO ASSISTED THORACIC SURGERY

(71) Applicants: Traves Crabtree, Springfield, IL (US); Timothy York, Edwardsville, IL (US); Mitch McKay, Glen Carbon, IL (US); Mingshao Zhang, Glen Carbon, IL (US)

(72) Inventors: Traves Crabtree, Springfield, IL (US); Timothy York, Edwardsville, IL (US); Mitch McKay, Glen Carbon, IL (US); Mingshao Zhang, Glen Carbon, IL (US)

(73) Assignee: Board of Trustees of Southern Illinois University, Carbondale, IL (US)

( * ) Notice: Subject to any disclaimer, the term of this patent is extended or adjusted under 35 U.S.C. 154(b) by 796 days.

(21) Appl. No.: 16/376,551

(22) Filed: Apr. 5, 2019

(65) Prior Publication Data
US 2019/0313028 A1    Oct. 10, 2019

Related U.S. Application Data

(60) Provisional application No. 62/653,845, filed on Apr. 6, 2018.

(51) Int. Cl.
*A61B 1/00* (2006.01)
*A61B 1/04* (2006.01)
(Continued)

(52) U.S. Cl.
CPC ....... *H04N 5/23296* (2013.01); *A61B 1/0004* (2022.02); *A61B 1/005* (2013.01);
(Continued)

(58) Field of Classification Search
CPC ..... A61B 1/0004; A61B 1/0016; A61B 1/005; A61B 1/0057; A61B 1/05; A61B 1/051;
(Continued)

(56) References Cited

U.S. PATENT DOCUMENTS 6,258,083 B1    7/2001    Daniel et al.
6,315,774 B1    11/2001    Daniel et al.
(Continued)

OTHER PUBLICATIONS

1. Kochowski M and Kozak J Video-Assisted Thoracic Surgery Complications Videosurgery and Other Miniinvasive Techniques 2014 pp. 495-500 vol. 9 No. 4.
(Continued)

*Primary Examiner* — Aaron B Fairchild
(74) *Attorney, Agent, or Firm* — Greer, Burns & Crain, Ltd.; Steven P. Fallon

(57) ABSTRACT

A multifunctional camera system having a bendable arm configured to be inserted into the thoracic cavity of a patient and camera head at a distal end of the bendable arm. The camera head has a high definition video camera and a light source. The camera head has a view adjustment mechanism for changing a view angle of the camera without changing the position of the camera head. A controller controls the view adjustment mechanism under command of a surgeon.

20 Claims, 7 Drawing Sheets

(51) Int. Cl.
*A61B 1/313* (2006.01)
*A61B 1/005* (2006.01)
*H04N 5/232* (2006.01)
*H04N 5/225* (2006.01)

(52) U.S. Cl.
CPC .......... *A61B 1/0016* (2013.01); *A61B 1/0057* (2013.01); *A61B 1/04* (2013.01); *A61B 1/313* (2013.01); *H04N 5/2256* (2013.01); *H04N 2005/2255* (2013.01)

(58) Field of Classification Search
CPC . A61B 1/00183; A61B 1/0051; A61B 1/0055; A61B 1/0058
See application file for complete search history.

(56) References Cited

U.S. PATENT DOCUMENTS

| | | |
|---|---|---|
| 7,099,717 B2 | 8/2006 | Woodard et al. |
| 7,751,870 B2 | 7/2010 | Whitman |
| 8,182,494 B1 | 5/2012 | Yencho et al. |
| 8,600,551 B2 | 12/2013 | Itkowitz et al. |
| 8,657,805 B2 | 2/2014 | Peh et al. |
| 8,740,895 B2 | 6/2014 | Mayse et al. |
| 2003/0130562 A1* | 7/2003 | Barbato ............ A61B 1/00183 348/E5.029 |
| 2004/0019348 A1 | 1/2004 | Stevens et al. |
| 2006/0149129 A1 | 7/2006 | Watts et al. |
| 2007/0249991 A1 | 10/2007 | Whayne et al. |
| 2011/0144438 A1 | 6/2011 | Paolitto et al. |
| 2013/0046137 A1 | 2/2013 | Zhao et al. |
| 2014/0012080 A1* | 1/2014 | Wada ................ A61B 1/00174 600/109 |
| 2015/0289755 A1 | 4/2015 | Voros et al. |
| 2016/0338573 A1 | 11/2016 | Aoki et al. |
| 2017/0078583 A1* | 3/2017 | Haggerty .......... A61B 1/00096 |

OTHER PUBLICATIONS

2. Reilink et al. Endoscopic Camera Control by Head Movements for Thoracic Surgery Proceedings of the 3rd IEEE RAS & EMBS International Conference on Biomedical Robotics and Biomechatronics 2010 pp. 510-515.

* cited by examiner

MULTIFUNCTIONAL CAMERA SYSTEM FOR VIDEO ASSISTED THORACIC SURGERY

PRIORITY CLAIM AND REFERENCE TO RELATED APPLICATION

The application claims priority under 35 U.S.C. § 119 and all applicable statutes and treaties from prior U.S. provisional application Ser. No. 62/653,845, which was filed Apr. 6, 2018.

FIELD

A field of the invention is surgical devices. The invention concerns a camera system for video assisted thoracic surgery.

BACKGROUND OF THE INVENTION

Video-assisted thoracoscopic surgery (VATS) is a type of thoracic surgery performed with the assistance of a small video camera that is introduced into the patient's chest, via one or more small incisions made specifically to introduce the camera or via a common opening through which surgical tools are also introduced. The camera allows the surgeon to view the instruments that are being used along with the anatomy on which the surgeon is operating. Most commonly, the camera and instruments are inserted through separate, 10 mm to 30 mm holes or "ports" in the chest wall. The small size of these ports corresponds with reduced prevalence of infection and wound dehiscence for VATS patients as compared to those subjected to thoracotomy, sternotomy, or other approaches that require large incisions to provide direct visual access to the surgeon. VATS patients thus enjoy shorter recovery times, reduced post-operative pain, and lower complication rates as compared to patients that undergo comparable non-VATS surgeries.

VATS came into widespread use beginning in the early 1990s. Operations that traditionally were carried out with thoracotomy or sternotomy that today can be performed with VATS include: biopsy for diagnosis of pulmonary, pleural or mediastinal pathology; decortication for empyema; pleurodesis for recurrent pleural effusions or spontaneous pneumothorax; surgical stapler assisted wedge resection of lung masses; resection of mediastinal or pleural masses; thoracic sympathectomy for hyperhidrosis; operations for diaphragmatic hernias or paralysis; esophageal resection or resection of esophageal masses or diverticula; and VATS lobectomy/mediastinal lymphadenectomy for lung cancer.

Similarly to laparoscopy, VATS has enjoyed widespread use for technically straightforward operations such as pulmonary decortication, pleurodesis, and lung or pleural biopsies. More technically demanding operations such as esophageal operations, mediastinal mass resections, or pulmonary lobectomy for early stage lung cancer are at present performed via VATS primarily at selected centers. It is expected, however, that the prevalence of advanced VATS techniques will continue to increase in response to patient demand and increased surgeon familiarity with the techniques.

Conventional camera systems for VATS typically include a camera-linked 5 mm or 10 mm fiber-optic scope and thoracic or laparoscopic instruments. Scopes commonly feature a 30-degree angle of visualization. Unlike with laparoscopy, carbon dioxide insufflation is not generally required with VATS due to the inherent vault-like shape of the thoracic cavity. However, lung deflation on the side of the chest where VATS is being performed is required to support visualization and allow for instruments to pass into the thorax. Lung deflation is usually accomplished with a double-lumen endo-tracheal tube that allows for single lung ventilation or a bronchial blocker delivered via a standard single-lumen endotracheal tube.

These conventional VATS camera systems feature long, rigid camera rods that are passed between a patient's ribs. This design introduces a number of challenges to both the surgical team and the patient. First, it is often necessary to create one or more separate incisions to accommodate the camera, with the surgeon operating from a separate port. The incisions themselves cause some amount of postoperative pain to the patient. Even for uniportal approaches (wherein the scope is inserted through the same incision that the surgeon operates through), pain can be exacerbated by intracostal nerve damage caused by manipulation and re-insertion of the rigid scope against the patients' rib bones. This damage can cause post-operative neuralgia and even induce chronic pain in some patients.

From the surgical team's perspective, conventional VATS scopes must be held and manually manipulated during the procedure. Even with such manipulation, it is often difficult to visualize the relevant structures due to the camera form factor. A camera at the end of a rigid rod may be sufficient for laparoscopic procedures that only require navigation around a patient's soft tissues. However, such designs are deficient for thoracic surgeries that necessitate navigation around the patient's ribs.

Conventional VATS are operated by a dedicated camera operator or an existing member of the surgical team. Dedicated operators add additional expense to the procedure, take up valuable room in the operating room, and often introduce additional barriers to the operational field itself, particularly for uniportal approaches that require both the camera operator and surgeon to work through the same small incision. Use of existing members of the surgical team as camera operators distracts them from their other duties in the operating room, and any camera operator may fail to manipulate the camera in a way that the surgeon prefers. Indeed, some surgeons prefer to operate their own cameras with one hand while performing surgery with the other.

A state-of-the art surgical robot with a camera is the da Vinci® surgical system. This system includes a tubular camera that is mounted to a robotic arm. Such a camera is poorly suited for thoracic surgery because of the limited space between the ribs with the cameras tubular shape. Current laparoscopic and robotic instrumentation designed for abdominal surgery is based on a circular port system, even for newer uniportal platforms. This is because there is no specific limitation in any particular direction when inserting ports into the abdomen. The circular or tubular design allows for the most efficient space for instrument insertion. In contrast, the spaces between the ribs, the intercostal spaces, are limited and vary widely based on the patients' body habitus. The intercostal space may range from approximately 5 mm up to 20 mm in width. A circular or tubular port will be restricted by the width of the intercostal space while the length of the intercostal space could better accommodate ports with more oblong shape or systems that provide a flat interface as the instruments or cameras enter between the ribs. The da Vinci® surgical system is therefore most often employed for other surgeries, including surgeries of the abdomen and pelvis.

SUMMARY OF THE INVENTION

A preferred embodiment is a multifunctional camera system for video-assisted thoracic surgery having a bendable arm configured to be inserted into the thoracic cavity of a patient and camera head at a distal end of the bendable arm. The camera head has a high definition video camera and a light source. The camera head has a view adjustment mechanism for changing a view angle of the camera without changing the position of the camera head. A controller controls the view adjustment mechanism under command of a surgeon.

DETAILED DESCRIPTION OF THE INVENTION

Figure 1A:
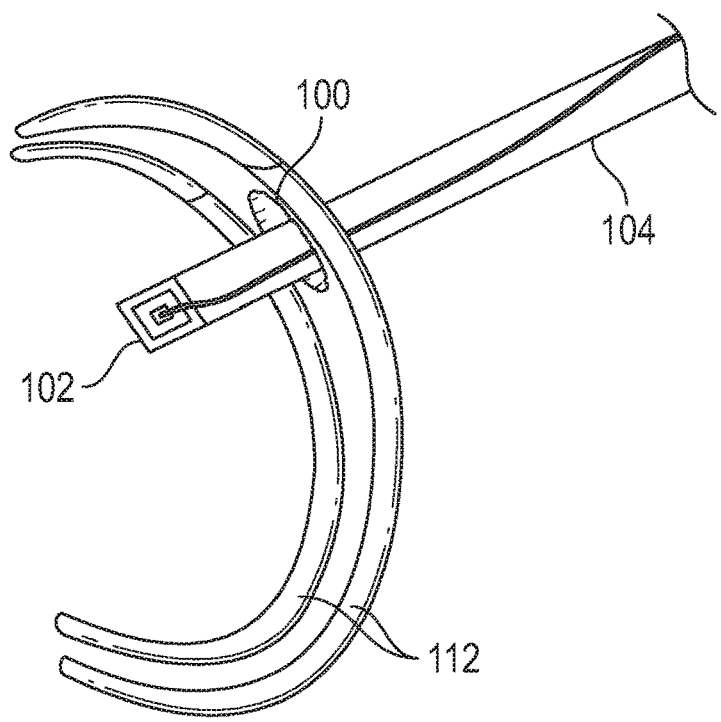
FIGS. 1A-1B are schematic views preferred embodiment camera systems being introduced into a patient's thoracic cavity.

A preferred embodiment is multifunctional camera system having a bendable arm configured to be inserted into the thoracic cavity of a patient and camera head at a distal end of the bendable arm. The camera head has a high definition video camera and a light source. The camera head has a view adjustment mechanism for changing a view angle of the camera without changing the position of the camera head. A controller controls the view adjustment mechanism under command of a surgeon. The controller can respond, for example, to voice-controlled activation. Preferably, the profile of the camera head is 20 millimeters or less, and preferably 10 millimeters or less.

The view adjustment mechanism can include a first substrate separated from a second substrate and an actuator that adjusts a relative angle between the first and second substrate. The first substrate can be a circuit board with the camera and the light source mounted thereupon. The actuator can be a spring between the first and second substrate and a plurality of tension cables connected to the first substrate. A conical spring can be centrally positioned between the first and second substrates. A plurality of springs can be positioned between corner portions of the first and second substrates. The tension cables can be routed through the second substrate and through the springs and through or along the flexible arm to a plurality of motors controlled by the controller. The motors can be stepper motors with spools or linear actuators. The view adjustment mechanism can also include a rotatable mount hub for rotating a plane of the camera head about a central axis.

The bendable arm is adjustable to a predetermined position by a surgeon and then retains that predetermined position to permit the surgeon to position the camera head flush with pleura or inner thoracic wall. The arm can include flexible rebar. A stabilizer can connect a portion of the flexible arm to the patient or another device.

The actuator can also be a pneumatic actuator between the first and second substrate. The pneumatic actuator can include pneumatic balloons, and system pneumatic lines routed through or along the flexible arm to a plurality of pneumatic pumps. With a plurality of balloons, each balloon can be positioned between separate quadrants of the first and second substrates.

Preferred systems of the invention provide improved visualization of the surgical field for surgeons performing VATS. Preferred systems can be patient-mounted, and provide hands-free view adjustment, which eliminates the need for a dedicated camera operator in surgery, reducing personnel cost and allowing the surgeon greater freedom of movement due to the lack of a camera operator near the incision. Hands-free operation can be achieved, for example, via voice activation (available by using commercial voice recognition software) could be one mechanism (i.e., the surgeon saying "left", "right", "up", or "down"). A foot pedal is another method of hands-free control. Automatic tracking is another option, where the camera view tracks the surgical instrument. Furthermore, the bendable arm used to secure the camera within the thoracic cavity reduces or eliminates potential intercostal nerve damage caused by pressure applied to rib bones while maneuvering conventional VATS cameras within the patient. This nerve damage can increase post-operative pain and cause chronic pain in some patients.

A preferred multifunctional camera system for video-assisted thoracic surgery features at least one small, high-definition video camera mounted on a flexible and adjustable arm. The arm is structured and configured to introduce the video camera into a surgical patient's thoracic cavity and place the camera against the patient's inner thoracic wall. The camera system also features at least one light source mounted adjacent to the video camera to illuminate the surgeon's field of view. At least one actuator allows the camera to roll, pan, and/or tilt so as to adjust the camera's field of view within the surgical field. A controller located outside the thoracic cavity is in electrical communication with the actuator. An optional camera cleaning mechanism allows blood or other materials that may obscure the camera view to be removed in-situ.

Preferred embodiments of the invention will now be discussed with respect to the drawings and experiments used to demonstrate the invention. The drawings may include schematic representations, which will be understood by artisans in view of the general knowledge in the art and the description that follows. Features may be exaggerated in the drawings for emphasis, and features may not be to scale.

Introduction and Positioning of Camera System in Thoracic Cavity

Figure 1B:
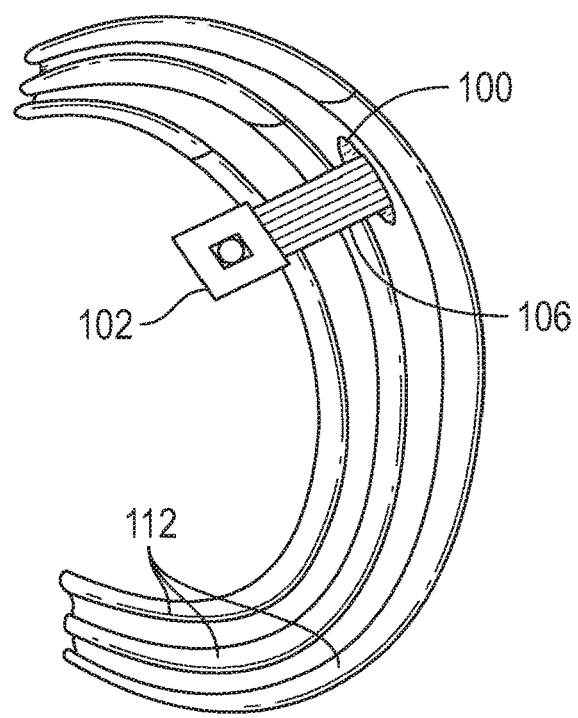
Figure 1C:
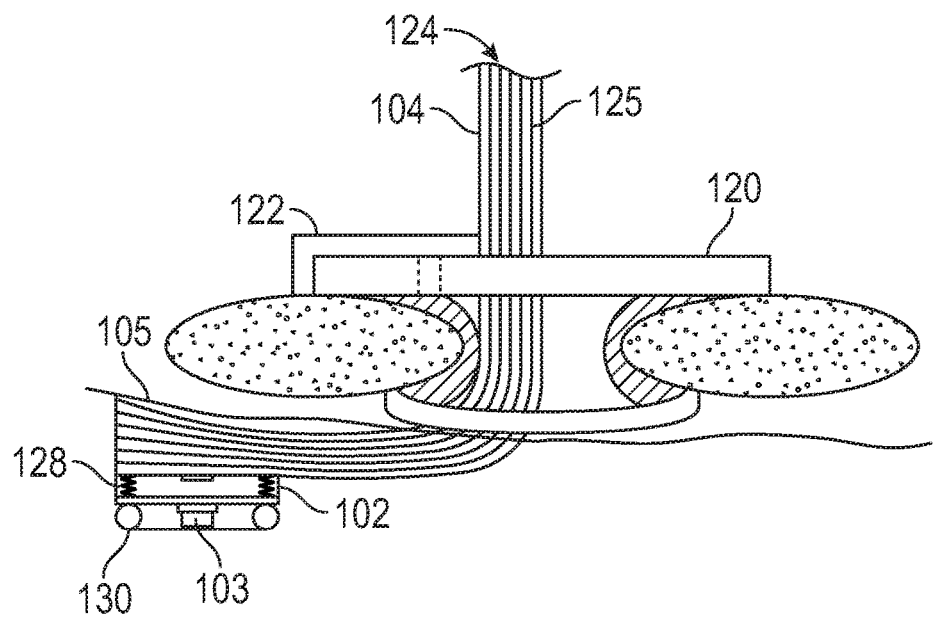
FIG. 1C is a schematic side view of an arm for a preferred embodiment camera system consistent with FIGS. 1A-1B in a bended state and clipped to a surgical stabilization device after insertion.

FIGS. 1A-1C illustrate a preferred embodiment multifunctional camera system for thoracic surgery through an incision 100 in a patient's rib cage. A camera head 102 with a camera 103 attached to an bendable arm 104 and a portion of camera cable 106 enters the thoracic cavity, preferably via the single primary working incision 100 between a patient's rib bones 112. The adjustable arm 104 is bendable into a shape that it then retains, so that it can be placed in a desired position to position the camera head. Any material that can be bent to a position and retain that shape is suitable. An example experimental system included an arm formed from aluminum that could be bent to conform around the rib bone. Because it is bent around the bone and retains that shape, it remains fixed during surgery, and thus does not contact the intercostal nerve like a rod camera that is being repositioned many times during surgery. The camera head 102 can be one or a plurality of camera heads attached to the flexible and adjustable arm 104. Similarly, the adjustable arm 104 can include or separate arms mounting separate camera heads 102. During a VATS procedure, video from the camera system is viewed by the surgeon in real time on one or more screens.

The camera head 102 is preferably low-profile and is positioned flush against the pleura or inner thoracic wall (105 in FIG. 1C) so as to maximize the surgeon-navigable volume within the patient's thoracic cavity. This surgeon-navigable volume typically spans 2 cm or less between the inner thoracic wall and the patient's organs. Initial placement of the camera head 102 is performed manually and comprises coarse adjustment of the camera view.

In a preferred embodiment, the arm 104 comprises flexible rebar that may be bent or molded prior to insertion. Such bending or molding allows the camera head's 102 position to be customized to accommodate variables such as patient physique, incision 100 location and size, surgical target, surgeon preference, etc. FIG. 1B shows another preferred embodiment wherein a camera cable 106 is attached to or adjacent to the arm 104. The arm 104 may be made of a non-structural aluminum alloy or some other material.

FIG. 1C shows that the camera head 102 can be secured in position against the inner thoracic wall by attaching the camera head 102 or arm 104 to a surgical stabilizing support device 120, such as an Alexis® Wound Protector/Retractor or a comparable purpose-made device. The arm 104 may be attached or mounted to the support ring 120 via a clip 122, clamp, adhesive, magnet, chain and cable, or other mechanism. The clip 122 can be attached to the patient or can be attached to the support ring 120 that holds the incision open. In an experimental prototype, the arm clipped to the support ring 120. Alternate approaches include an external mount/platform that is used to move the arm 104 into the desired position and then the mount/platform is stable.

The surgical stabilizing device may be circular, oblong, or some other shape. Tension cabling 124 within or along the arm 104 can adjust the view the camera 103 while the camera head 102 remains flush against the inner thoracic wall. The tension cabling 124 adjusts portions of the camera head 102 to adjust the view of the camera 103. The arm 104 remains in a fixed position and a portion of the camera head 102 remains positioned against the thoracic wall 105, while the camera view is adjusted. The tension cabling 124 adjusts movable portions of the camera head 102. Springs 128 can change the angle of the camera head 102 and are controlled by an external motor or linear actuator. A cleaning mechanism 130 can be realized by a movable film across a lens of the camera 103 and serves to keep the lens free of debris such as blood during surgery. Once moved into the position flush on the thoracic wall, the camera head 102 is held in place by the friction and normal forces exerted on the arm 104 by the surgical stabilizing device and the patient's body adjacent to the incision 100. In this position, the tilt of the camera head can be changed by adjusting springs 128.

Figure 2A:
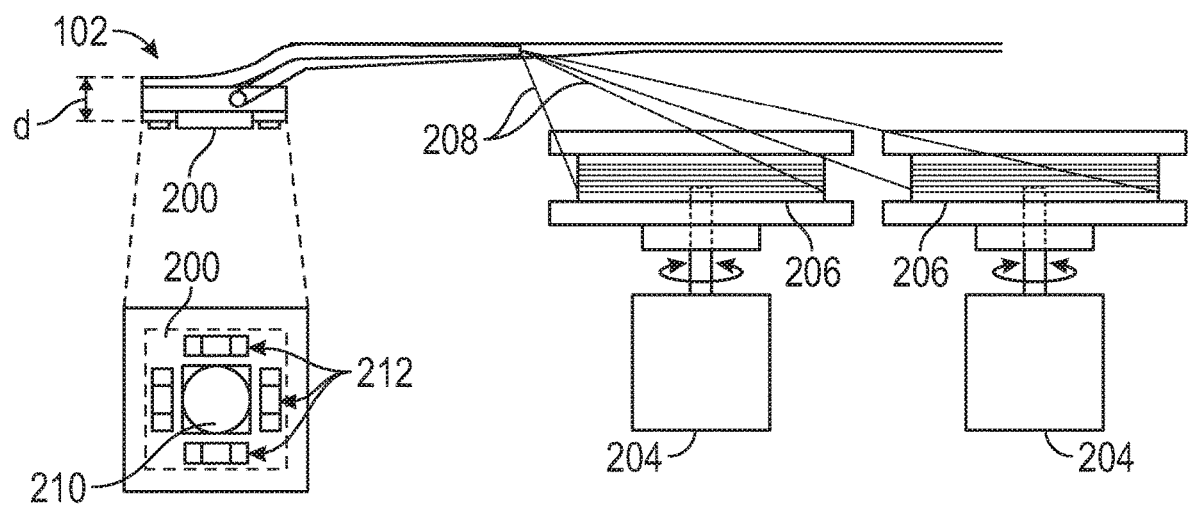
FIGS. 2A-2C illustrate a preferred embodiment camera system view adjustment mechanisms and actuators.

FIG. 2A shows details of a preferred camera 200 portion of the camera head 102 and additional features of a preferred camera system. Two or more stepper motors 204 rotate spools 206 to control tensioning cables 208, which serve to adjust the view. Four tensioning cables 208 are shown in FIG. 2A, and two stepper motors can operate differentially to control the four cables or four motors can be used to independently control the four tensioning cables 208. The camera portion 200 includes a one or more small, high-definition video cameras 210 and one or more light sources 212, preferably LEDs. The high-definition video cameras 210 preferably feature full-spectrum color sensing capabilities and a resolution of at least 1280×720 pixels. The signal cables 125 (shown in FIG. 1C) include power/data wires for the camera(s) 210, the light sources 212, pan-tilt apparatus (e.g. springs 128), and/or the cleaning apparatus 130. The arm 104 can also carry or house tubes or vessels to convey cleaning solution to the camera head 102; tubes or vessels to convey fluid to or from a pneumatic pan/tilt apparatus; or the tension cables connecting mechanical pan/tilt apparatus to external motors or controls.

The view of the camera(s) 210 can be adjusted, preferably in multiple ways such that a surgeon can control the view without needing to reposition the arm 104. View adjustments can include translation of the entire camera head 102 so as to shift the camera view laterally or tilting and rolling of the camera portions 200 or its constituent high-definition video camera(s) 210. Any or all of these view adjustments can be implemented separately or together. A preferred embodiment includes all of the view adjustments. The view adjustment portion of the system can be very low profile. The substrates, mechanical portions, and actuators are preferably 10 cm or less in profile, which limits trauma during introduction and minimally obstruct the incision space and occupy a minimal portion of the thoracic cavity during surgery.

Figure 2B:
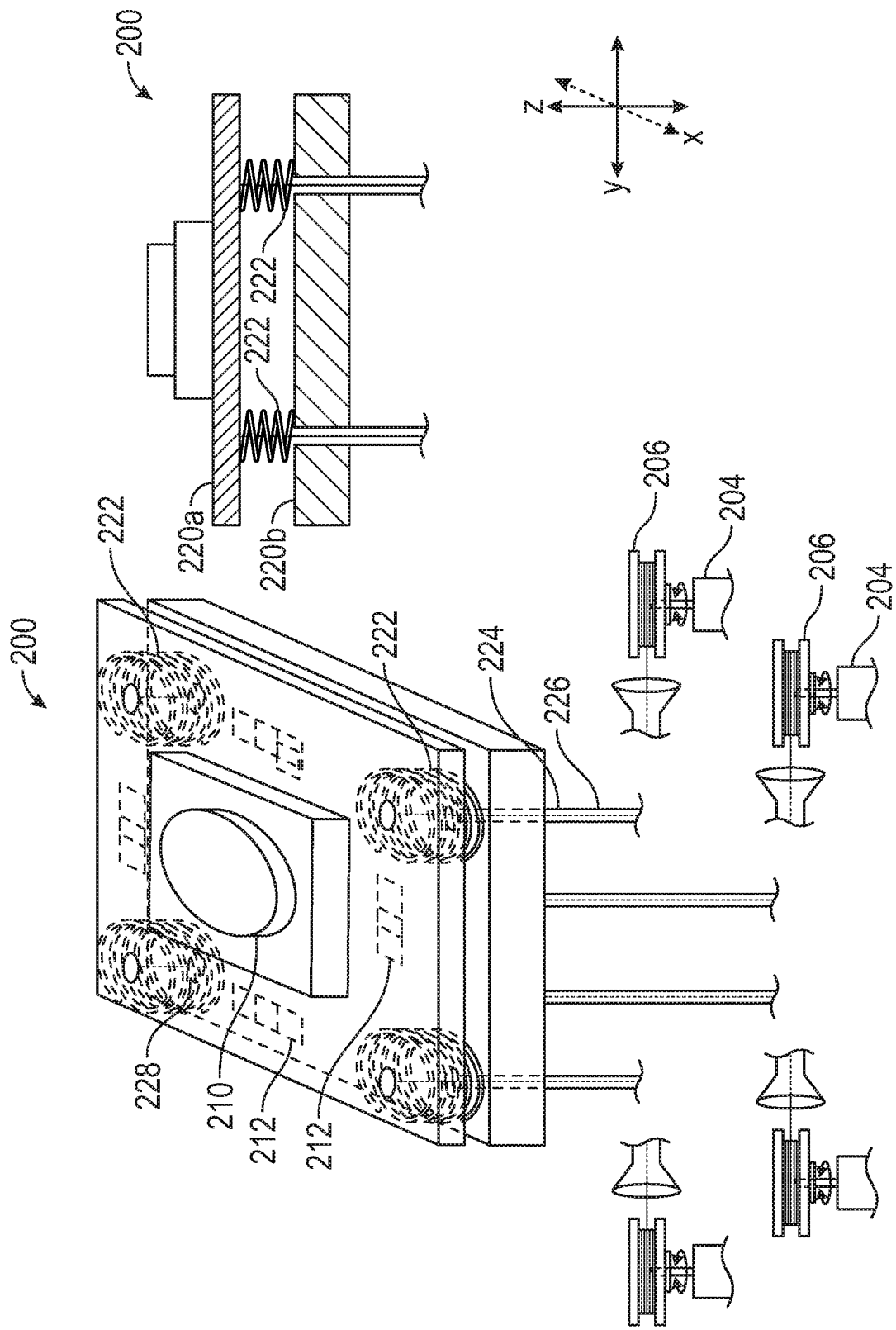

FIG. 2B shows a preferred view adjustment for the camera system of FIG. 2A. In FIG. 2B, the camera portion 200 includes two substrates 220a, 220b that are separate from each other by four springs 222, at four corners of the two substrates. The top substrate 220a is a circuit board holding the camera 210 and light sources 212 has its underside attached to the four cylindrical springs 222. Tension cables 224, such as Bowden cables, having sheaths 226 are affixed to the underside or bound through a hole in top substrate/circuit board 220s. The cables 224 are affixed near to or, more preferably through the center of each spring 222. The tension cables 224 pass through holes 228 in the lower substrate 220b that serves as a backing for the springs. The springs 222 can be mounted around the through holes 228, and have larger diameters than the through holes 228 in that instance. The backing plate 220b may be a separate plate attached to the arm 104, but can also be formed as a unitary or integrated end of the bendable mounting arm itself The cable sheaths 226 are affixed to the underside of the mounting plate/lower substrate 220b, with the tension cables 224 running through the sheaths 226, as in a Bowden cable. The sheath 226 from each spring 222 and cable 224, along with the power and signaling for the camera and lighting are routed along the mounting arm 104, such as inside a sheath that covers the arm 104 or inside the arm itself The tension cables 224 are attached to the computer-controlled stepper motors 204, which individually adjust the amount of tension in each of the four springs 222. This changes the view of the camera 210 via tilt about the z-x plane (left-right on the displayed image) or z-y plane (up-down on the displayed image) with the z-axis normal to the center of the camera lens. Linear actuators can be used instead of the spools 206. Changing the tension of individual ones of the springs 222 causes compression or decompression to cause the camera 210 to tilt about the z-axis normal to the center of the camera lens in the z-x plane (left-right) or z-y plane (up-down). The springs 224 can be compressed by pulling the tension cables tight, preferably the default state as provides the thinnest profile for the camera head during insertion. The external motors 204 can then selectively release the tension for any of the four springs 222 to move adjust the camera view by changing the angle of the top substrate 220a.

In the following example view adjustments, "right" and "left" can be assigned arbitrarily but are opposite to each other, and are adjacent to "up" and "down". Looking furthest to the left would have two cables on left side maximally tight and the two on the right side minimally tight. A maximum right adjustment is achieved by tightening the right springs by pulling the cable while releasing tension on the left springs. Positions between maximum and minimum tensions provide steps between maximum left and maximum right view. Similarly, adjusting tension in springs on up and down sides adjusts the view up and down. Adjusting tension in opposite corners provides a combination of view adjustment, e.g., up and left.

Figure 2C:
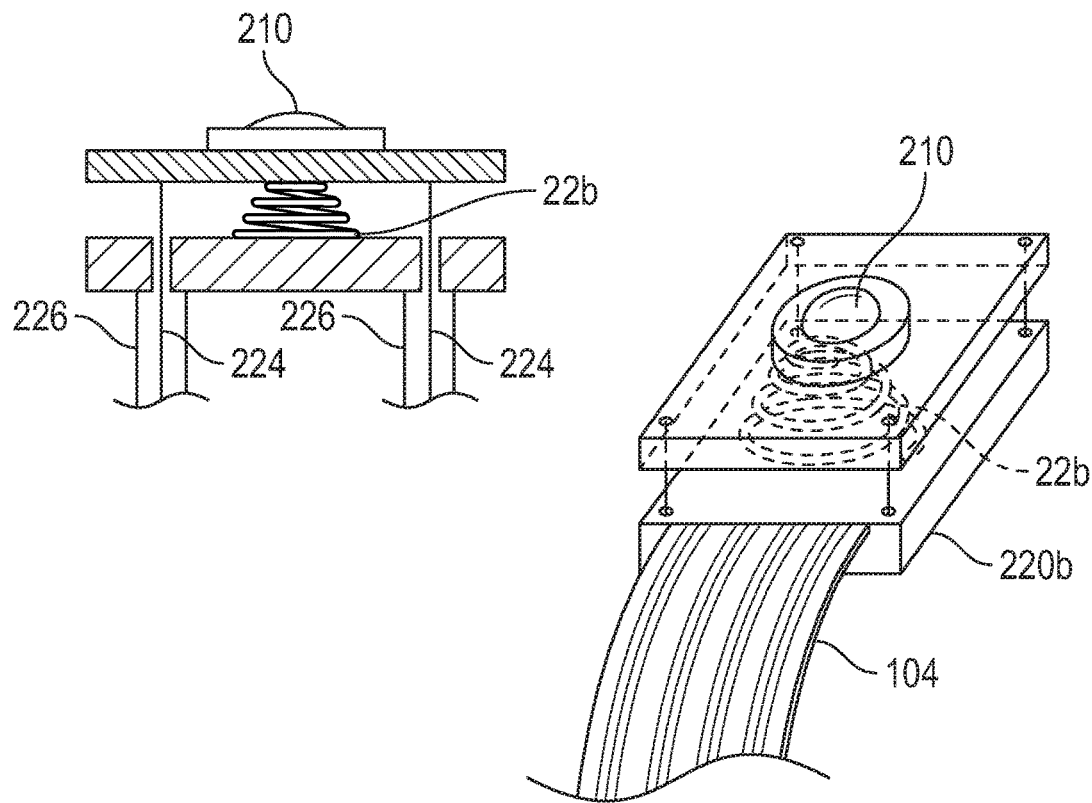

FIG. 2C shows another view adjustment mechanism. The FIG. 2C via adjustment is similar to the adjustment in FIG. 2B, but replaces the four springs 222 with a centrally positioned conical spring 222b. The wider base of the conical spring is affixed to the backing plate 220b. The narrower tip is affixed to the underside of the camera circuit board 220a. As in FIG. 2B, the tension cables 224 are affixed to the underside of the camera circuit board 220a or bound through holes in the circuit board 220a. The cabling is routed through holes 228 in corner portions of the backing plate 220b. Differentially compressing the spring allows for movement of the camera 210 in the z-x plane (left-right) or z-y plane (up-down).

Figure 3A:
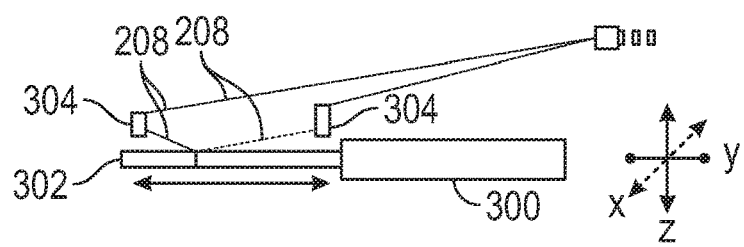
FIGS. 3A and 3B illustrate a linear piston-based actuation for view adjustment.
Figure 3B:
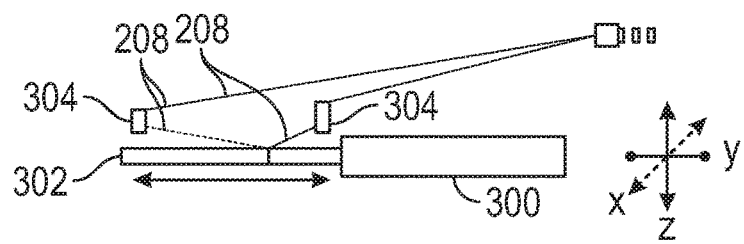

FIGS. 3A and 3B show another view adjustment mechanism for the camera system of FIG. 2A. A liner actuator 300 moves a piston 302 bidirectionally. At least one, and preferably two, anchors 304 route cables 208, which extend along/through the arm 104 into the patient cavity and are attached to a mounting platform as in FIGS. 2A-2C.

Figure 4:
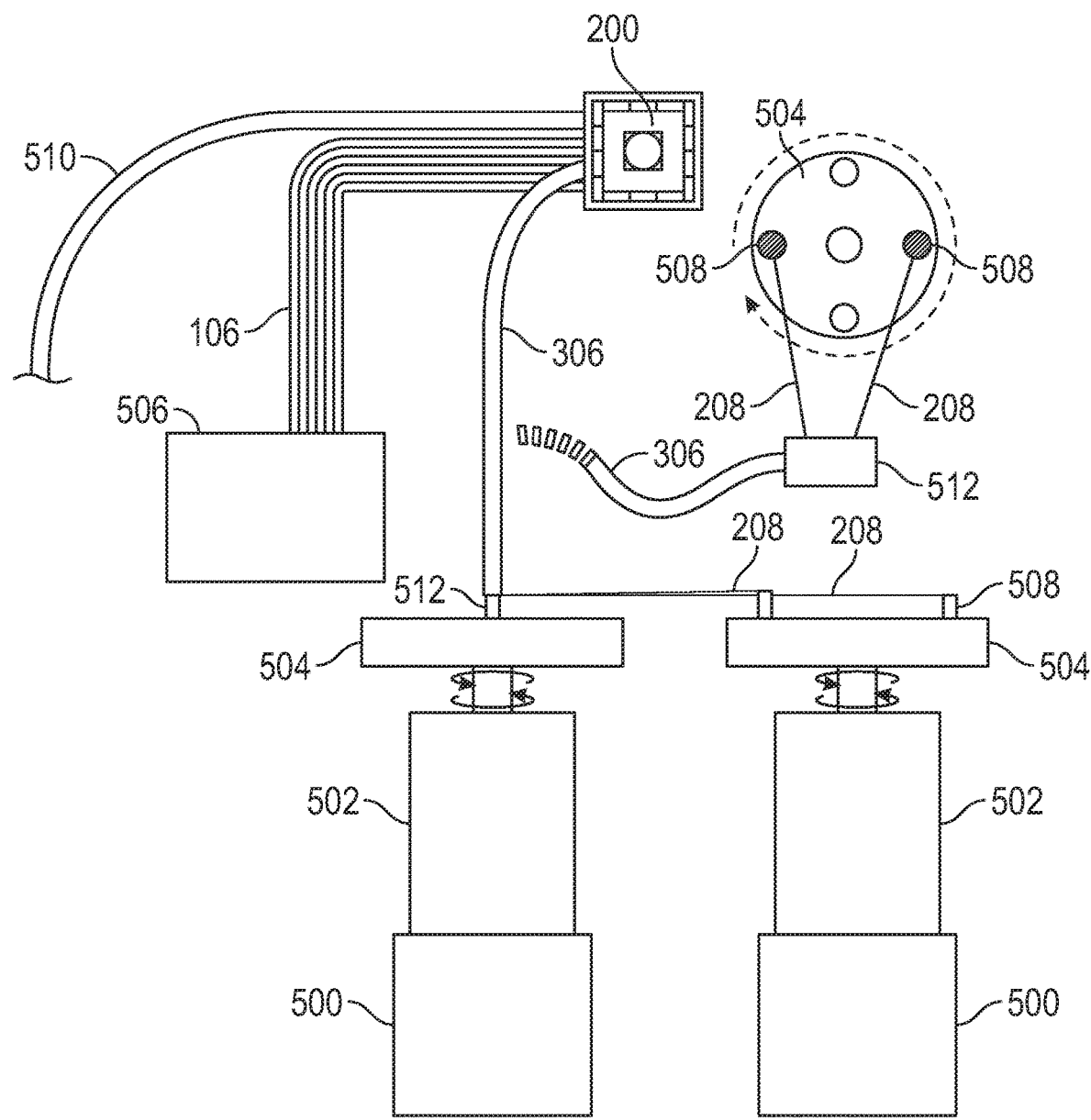
FIG. 4 illustrates a system with rotational view adjustment.
Figure 5:
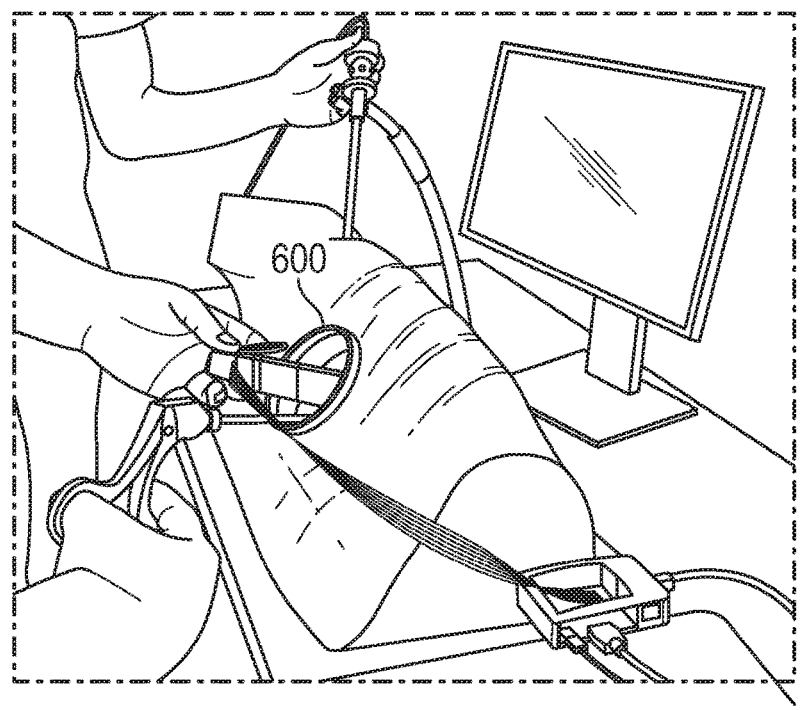
FIG. 5 illustrates a prototype camera system in accordance with a preferred embodiment in a surgical training environment.

For a rotational adjustment, as shown in FIG. 4, motors 500 are each in communication with a gearbox 502, with each gearbox 502 also in communication with a mount hub 504 which is in turn also in communication with cables 208. The mount hub 504 can be the substrate 220b, which would then be mounted rotationally on an additional substrate 512 that is stationary with respect to the thoracic wall 105. The motors 500 may be stepper motors, brushless DC motors, servos, or any other device capable of moderating tension on the cables 208. In FIG. 5, the motor on the left is configured to rotate the camera head 102 about an axis corresponding to the arm/cable housing. In this embodiment, the cable housing 306 is attached to the mount hub 504 via the additional substrate 512.

FIG. 4 also illustrates a computer controller 506 which may be connected to the camera portion 200 via electric wires 106 which may comprise a ribbon cable. The electrical wires 106 may also or alternatively be attached to a readout board or a motor controller. The computer controller 506 is also connected to the motors 500 in a typical embodiment, and the controller can also control the other view adjustments of FIGS. 2B-3B. A mount hub 504 featuring attachment mechanisms 508 such as screws can secure the tension cables 208. The tension cable control system as shown in FIG. 4 features an irrigation tube 510 that can be used to direct a biocompatible fluid onto the camera portion 200 to remove blood or other debris which may obscure the camera view. FIG. 5 illustrates a prototype implementation, in a surgical training environment, of a tension cable control system featuring rotational actuation that is attached to a support ring 600.

Figures 6A, 6B:
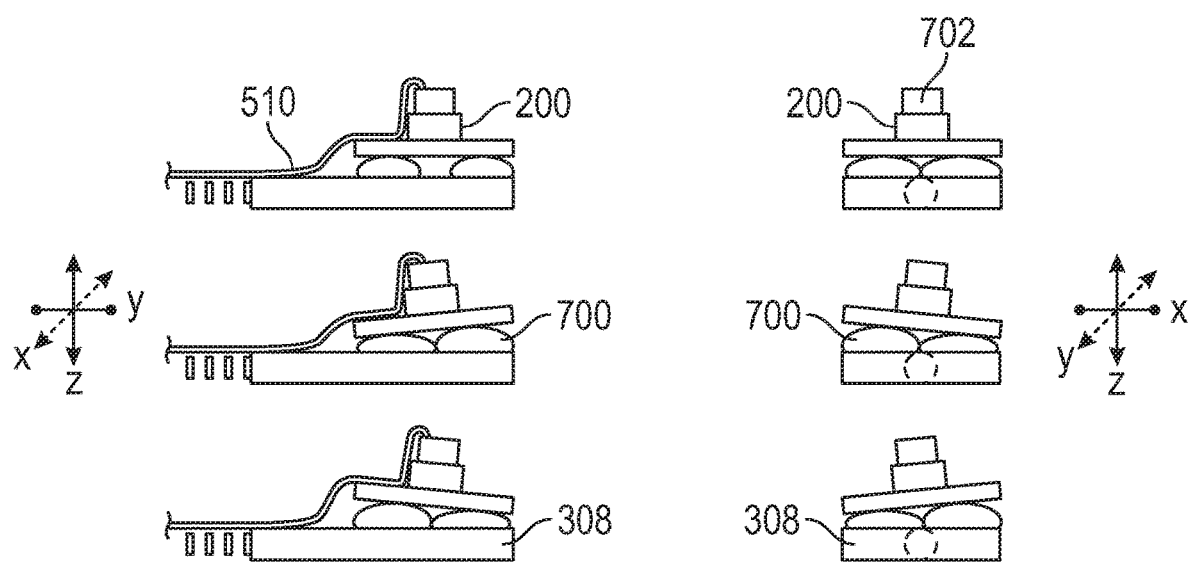
FIGS. 6A and 6B illustrate another preferred view adjustment including pneumatic balloon actuators.

Other view adjustment mechanisms can feature pneumatic actuation, as opposed to tension cable manipulation, to effect adjustment of the camera view. FIGS. 6A-6B shows a camera head 102 for a pneumatic-actuated system wherein the camera portion 200 is mounted on top of one or more pneumatic balloon actuators 700. In FIGS. 6A-6B, the z axis is parallel to the normal to the camera portion 200 when the unit is in a neutral position and the y axis is parallel to the arm 104. Angling of the camera view may be achieved by inflating or deflating the balloon actuators 700, which in turn increases or decreases the distance between the camera portion 200 and the mounting platform 308 (alternatively, the camera portion 200 may be positioned directly on the mounting platform 308 and the balloon actuators 700 directly on the arm 104). When one or more balloon actuators 700 are positioned away from the center of the camera portion 200, such increases or decreases in distance between the camera portion 200 and mounting platform 308 serve to angle the camera portion 200 relative to the mounting platform 308. In a typical embodiment, the camera portion may be angled up to 20 degrees from the z axis.

The camera head 102 as shown in FIGS. 6A-6B features four balloon actuators 700 arranged in a two- by-two configuration that allows the camera portion 200 to be angled 360 degrees within the x-y plane (e.g. the camera portion 200 can both tilt and roll). Alternative embodiments may feature more or fewer balloon actuators 700 or may use a bellows in place of the balloon actuators. For example, a single actuator located to one side of the mounting platform 308 and camera portion 200 may be deflated to angle the camera portion 200 in one direction, fully inflated to angle the camera portion 200 in the opposite direction, or partially inflated to return the camera portion 200 to its normal viewing angle. With such a configuration, two balloon actuators 700 may be sufficient to allow for angling about the full 360 degrees of the x-y plane. Likewise, a higher number of balloon actuators 700 may offer increased control or redundancy.

Figure 7:
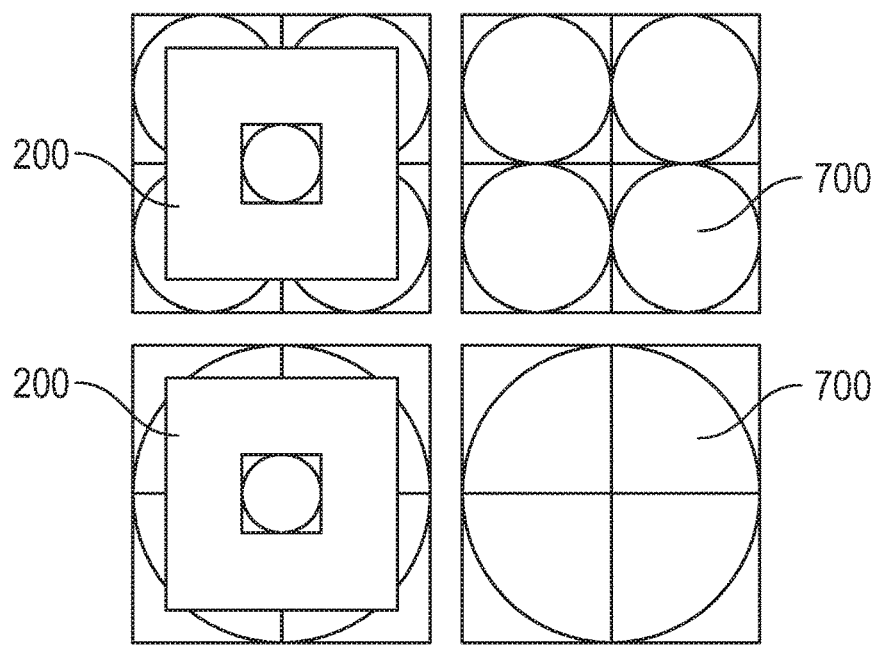
FIG. 7 illustrates pneumatic balloon actuator cross-sections.

The balloon actuators 700 can be selected from a variety of cross-sections. FIG. 7 shows balloon actuator 700 variations featuring both circular (top) and pie-shaped (bottom) cross sections. Control of pneumatic actuators is analogous to the embodiment shown in FIG. 2B, except the motors 204 and spools 206 are replaced by an air pump and the cables 208 are replaced by lines that convey pneumatic fluid to the actuators 700. Two bi-directional pumps may suffice to operate one four-balloon 700 system by implementing differential inflation.

Another type of actuator that can be used is a piezoelectric actuators. Such actuators also can adjust the view angle in place of springs or pneumatic balloons and can be triggered to adjust the camera viewing angle merely via electrical signals.

The camera systems of the invention may be controlled by the surgeon or an assistant manually, using voice control, or using eye tracking capabilities. Microsoft® has a speech API built in to Windows® and Dragon Naturally Speaking® are examples for speech recognition programs to convert speech comments to control. Stryker has a voice control package (SDC3) for medical equipment. Open source solutions include the Carnegie Mellon Sphinx library, and the Kaldi library. Alternatively, camera system control may be automated by, for example, causing the camera(s) to track surgical tools introduced to the thoracic cavity. Google Glass, the Microsoft Hololens, and products like the Tobii can be leveraged. Manual control may be achieved by a joystick, a remote with physical buttons, a mobile application for a touch-screen device, control mechanisms built into the surgical tools, or some other means. In a preferred embodiment, the camera system features automated control with a manual override.

Preferred embodiments feature hardwired connections between the camera head 102 components and power supplies, processors, and controllers. Other preferred embodiments feature modified camera heads 102 that have: a first portion that is introduced into the thoracic cavity comprised of one or more high-definition video cameras, one or more light sources, an optional mounting apparatus 308, any necessary actuators 300, and a cleaning apparatus; and a second portion that is in physical and electrical communication with the first portion but is not introduced to the thoracic cavity comprised of signal transmission hardware and a power source.

Cleaning of Camera Lens

Over the course of a VATS procedure, the camera portion 200 typically will become at least partially obscured with blood or other bodily fluids. FIGS. 6A-6B shows a portion of one such embodiment that comprises an irrigation tube 510 positioned to rinse the camera lens 702 with a biologically compatible fluid. In this embodiment, the irrigation tube is connected to a reservoir containing the biologically compatible fluid, where such reservoir would preferably be located outside the patient's thoracic cavity.

Figure 8:
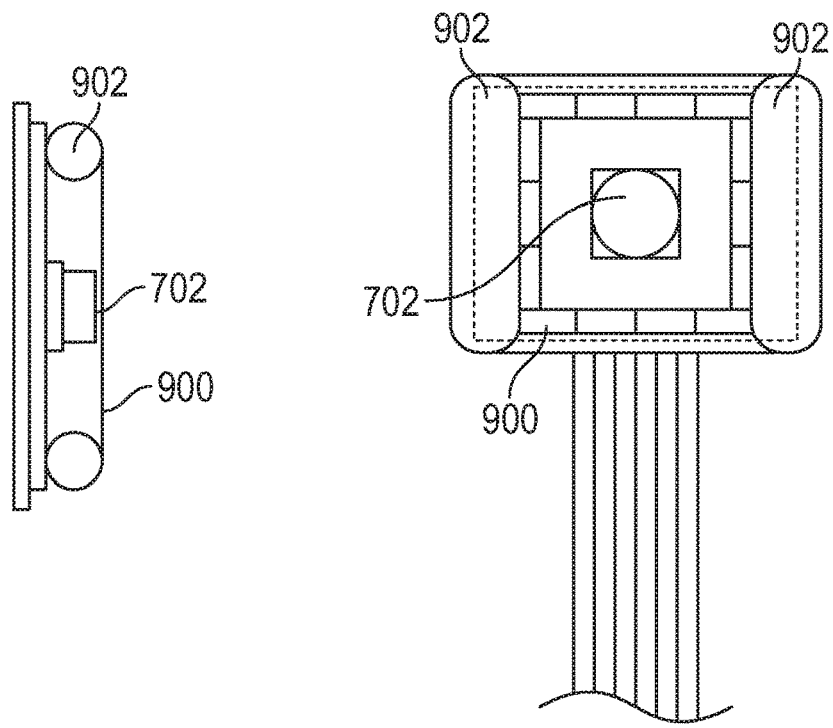
FIG. 8 illustrates a lens cleaning apparatus featuring a biocompatible film on piezoelectric-actuated rollers a preferred embodiment camera system.

Another cleaning mechanism shown in FIG. 8 and features a transparent biocompatible film 900 that is arranged over the camera lens 702. In one embodiment, one or two rollers 902 may be used to translate the film 900 across the camera lens 702. Translation enables the soiled, view-obscuring portion of film to be moved such that a non-soiled portion of film covers the lens 702. Such translation may be realized via piezoelectric or some other form of actuation. Preferably, such action is automated with optional manual override.

In preferred embodiments, the camera system features a disposable camera head 102 and an adjustable arm 104 that is either disposable or can be sterilized. Most or all camera system components that are not introduced to the thoracic cavity may be sterilized and used for multiple procedures. In other embodiments, the camera head is encased in a water- and steam-proof layer that allows for sterilization and re-use of the camera head 102.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A multifunctional camera system for video-assisted thoracic surgery comprising a bendable arm configured to be inserted into a thoracic cavity of a patient and camera head at a distal end of the bendable arm, wherein the camera head comprises a high definition video camera and a light source, the camera head further comprising a view adjustment mechanism for changing a view angle of the camera without changing a position of the camera head, and a controller for controlling the view adjustment mechanism in response to commands of a surgeon.

2. The system of claim 1, wherein the view adjustment mechanism comprises a first substrate separated from a second substrate and an actuator configured to adjust a relative angle between the first and second substrate.

3. The system of claim 2, wherein the first substrate is circuit board with the camera and the light source mounted thereupon.

4. The system of claim 2, wherein the actuator comprises a spring between the first and second substrate and a plurality of tension cables connected to the first substrate.

5. The system of claim 4, wherein the spring comprises a conical spring centrally positioned between the first and second substrates.

6. The system of claim 4, wherein the spring comprises a plurality of springs positioned between corner portions of the first and second substrates.

7. The system of claim 6, wherein the tension cables are routed through the second substrate and through the springs.

8. The system of claim 4, wherein the tension cables are routed through or along the bendable arm to a plurality of motors controlled by the controller.

9. The system of claim 8, wherein the motors comprise stepper motors with spools.

10. The system of claim 8, wherein the motors comprise linear actuators.

11. The system of claim 2, wherein the actuator comprises a pneumatic actuator between the first and second substrate.

12. The system of claim 11, wherein the pneumatic actuator comprises pneumatic balloons, and the system comprises pneumatic lines routed through or along the flexible arm to a plurality of pneumatic pumps.

13. The system of claim 11, wherein the pneumatic balloons comprise a plurality of balloons, with each balloon being positioned between separate quadrants of the first and second substrates.

14. The system of claim 1, wherein the view adjustment mechanism comprises rotatable mount hub for rotating a plane of the camera head about a central axis.

15. The system of claim 1, wherein the bendable arm is configured to adjust to a predetermined position by a surgeon and configured to retain that predetermined position to permit the surgeon to position the camera head flush with pleura or inner thoracic wall.

16. The system of claim 15, wherein the flexible arm comprises flexible rebar.

17. The system of claim 1, further comprising a stabilizer for connecting a portion of the flexible arm to the patient.

18. The system of claim 1, wherein the controller is configured for voice-controlled activation.

19. The system of claim 1, wherein a profile of the camera head is 20 millimeters or less.

20. A multifunctional camera system for video-assisted thoracic surgery comprising a bendable arm configured to be inserted into a thoracic cavity of a patient and camera head at a distal end of the bendable arm, wherein the camera head comprises a high definition video camera and a light source, the camera head further comprising view adjusting means for adjusting a view angle of the camera without changing a position of the camera head.

* * * * *